(12) United States Patent
Shioyama

(10) Patent No.: US 8,965,551 B2
(45) Date of Patent: Feb. 24, 2015

(54) DEFECT ANALYZING METHOD AND DEFECT ANALYZING APPARATUS

(75) Inventor: Yoshiyuki Shioyama, Yokkaichi (JP)

(73) Assignee: Kabushiki Kaisha Toshiba, Tokyo (JP)

(*) Notice: Subject to any disclaimer, the term of this patent is extended or adjusted under 35 U.S.C. 154(b) by 460 days.

(21) Appl. No.: 13/050,191

(22) Filed: Mar. 17, 2011

(65) Prior Publication Data

US 2012/0046778 A1     Feb. 23, 2012

(30) Foreign Application Priority Data

Aug. 20, 2010   (JP) ................................ P2010-185373

(51) Int. Cl.
    G06F 19/00    (2011.01)
    H01L 21/66    (2006.01)
    G01N 21/95    (2006.01)

(52) U.S. Cl.
    CPC ............ *H01L 22/12* (2013.01); *G01N 21/9501* (2013.01); *H01L 22/20* (2013.01)
    USPC .......................................... 700/110; 700/96

(58) Field of Classification Search
    USPC .................................................. 700/96, 110
    See application file for complete search history.

(56) References Cited

U.S. PATENT DOCUMENTS

| 5,886,909 A * | 3/1999 | Milor et al. ..................... 716/52 |
| 7,100,146 B2 | 8/2006 | Sato et al. |
| 2006/0092420 A1* | 5/2006 | Oishi ............................ 356/401 |
| 2007/0054809 A1* | 3/2007 | Kawakami ..................... 505/100 |

FOREIGN PATENT DOCUMENTS

| JP | 2000-222118 | 8/2000 |
| JP | 2007-36068 | 2/2007 |

OTHER PUBLICATIONS

Notice of Reasons for Rejection issued by the Japanese Patent Office on Dec. 4, 2012, for Japanese Patent Application No. 2010-185373, and English-language translation thereof.

* cited by examiner

*Primary Examiner* — Carlos Ortiz Rodriguez
(74) *Attorney, Agent, or Firm* — Finnegan, Henderson, Farabow, Garret & Dunner, L.L.P.

(57) ABSTRACT

A defect analyzing method includes acquiring a position and a size of a defect obtained in a defect inspection of a semiconductor device and a waveform of a reflected light in a region which includes the defect, the waveform being obtained in an optical inspection; acquiring process step information which includes a plurality of process steps to manufacture the semiconductor device and a processing content per the process step; performing a process simulation of the semiconductor device based on the position and the size of the defect and the process step information; performing an optical simulation on a result of the process simulation thereby to generate a waveform of a reflected light; calculating a similarity degree between the acquired waveform of the reflected light and the generated waveform of the reflected light; and judging whether or not the calculated similarity degree exceeds a threshold value registered in advance.

5 Claims, 17 Drawing Sheets

<LID 123456>
<MODEL NAME ABCDE>

| PROCESS STEP No | PROCESS STEP NAME | CONTENT |
|---|---|---|
| No.1 | SACRIFICE OXIDE FILM FORMATION | Tox=10±1nm |
| No.2 | FILM THICKNESS MEASUREMENT 1 | |
| No.3 | NITIRDE FILM DEPOSITION | Tsin=120±12nm |
| No.4 | FILM THICKNESS MEASUREMENT 2 | |
| No.5 | POLY-SILICON DEPOSITION | Tpoly=30±3nm |
| No.6 | FILM THICKNESS MEASUREMENT 3 | |
| No.7 | DEFECT INSPECTION 1 | |
| No.8 | RESISTAPPLICATION | Tresist=300±30nm |
| No.9 | SDG EXPOSURE(LITHOGRAPHY) | |
| No.10 | DEVELOPMENT | |
| No.11 | DIMENSION MEASUREMENT 1 | L/S=100±10/100±10nm |
| No.12 | ANISOTROPIC ETCHING | JUST+30% |

| Etching Film | OXIDE FILM | PolySi | NITIRIDE FILM | Resist |
|---|---|---|---|---|
| Etch Rate[nm/min] | 120±12 | 50±10 | 100±10 | 30±3 |

| | | |
|---|---|---|
| No.13 | RESIST PEALING | |
| No.14 | DEIMENSION MEASUREMENT 2 | L/S=90±9/110±11nm |
| No.15 | DEFECT INSPECTION 2 | |

FIG. 5

| | | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|---|
| N0000_DefineDefect | X0 | | | | | | | | | | 0.1 | | | | | | | | | |
| | Dsize | | | | | | | | | | 0.03 | | | | | | | | | |
| | Dmat | | | | oxide | | | | | | nitride | | | | | | PolySi | | | |
| N0010_PadOx | Tox | | | | 10 | | | | | | 10 | | | | | | 10 | | | |
| | N0010 | 0 | | | 0 | | | 1 | | 0 | | | 1 | | 0 | | 0 | | 1 | |
| N0020_PadSiN | Tsin | 120 | | | 120 | | | 120 | | 120 | | | 120 | | 120 | | 120 | | 120 | |
| | N0020 | 0 | | | 0 | | | 0 | | 0 | | | 0 | | 0 | | 0 | | 0 | |
| N0030_PadaSi | Tpoly | 30 | | | 30 | | 30 | | | 30 | | | 30 | | 30 | | 30 | | 30 | |
| | N0030 | 0 | | 1 | 0 | | 0 | 0 | 0 | 0 | | | 0 | 0 | 0 | | 0 | | 0 | 0 |
| N0040_AALitho | Tresist | 300 | | | 300 | 300 | 300 | 300 | 300 | 300 | | 300 | 300 | 300 | 300 | 300 | 300 | 300 | 300 | 300 |
| | N0040 | 0 | 1 | | 0 | 0 | 0 | 0 | 0 | 0 | 1 | | 0 | 0 | 0 | 1 | 0 | 0 | 0 | 0 |
| N0050_HMRIE | HMRIEOE | 30 | 30 | | 30 | 30 | 30 | 30 | 30 | 30 | 30 | | 30 | 30 | 30 | 30 | 30 | 30 | 30 | 30 |
| | N0050 | 0 | 0 | | 0 | 0 | 0 | 0 | 0 | 0 | 0 | | 0 | 0 | 0 | 0 | 0 | 0 | 0 | 0 |

FIG. 15

DEFECT ANALYZING METHOD AND DEFECT ANALYZING APPARATUS

CROSS-REFERENCE TO RELATED APPLICATION

This application is based upon and claims the benefit of priority from the prior Japanese Patent Application No. 2010-185373, filed on Aug. 20, 2010; the entire contents of which are incorporated herein by reference.

FIELD

Embodiments described herein relate generally to a defect analyzing method and a defect analyzing apparatus for a semiconductor device.

BACKGROUND

In order for improvement of a yield of a semiconductor device, it is important to detect an abnormality of the semiconductor device in early stages by an inspection apparatus and, after analyzing a cause of the abnormality, to feedback to a relevant manufacturing apparatus. Thus, in manufacturing process steps of the semiconductor device, a film thickness, a size, a shape and so on in a specific place in the semiconductor device are inspected per several process steps to several tens of process steps, and if a defect exists, that defect is feedbacked to a manufacturing line. As what is related to a yield of a semiconductor device, there is one in which a degree (a size and the number) of a foreign object generated in a manufacturing line is predicted and to estimate a yield of a semiconductor device in that manufacturing line.

BRIEF DESCRIPTION OF THE DRAWINGS

FIG. 5 is a process step flow diagram stored in a process step flow DB.

FIGS. 12 to 15 are views illustrating examples of an input screen.

DETAILED DESCRIPTION

A defect analyzing method according to embodiments includes: acquiring a position and a size of a defect obtained in a defect inspection of a semiconductor device and a waveform of a reflected light in a region which includes the defect, the waveform being obtained in an optical inspection; acquiring process step information which includes a plurality of process steps to manufacture the semiconductor device and a processing content per the process step; performing a process simulation of the semiconductor device based on the position and the size of the defect and the process step information; performing an optical simulation on a result of the process simulation thereby to generate a waveform of a reflected light; calculating a similarity degree between the acquired waveform of the reflected light and the generated waveform of the reflected light; and judging whether or not the calculated similarity degree exceeds a threshold value registered in advance.

Hereinafter, embodiments of the present invention will be described in detail with reference to the drawings.

First Embodiment

Figure 1:
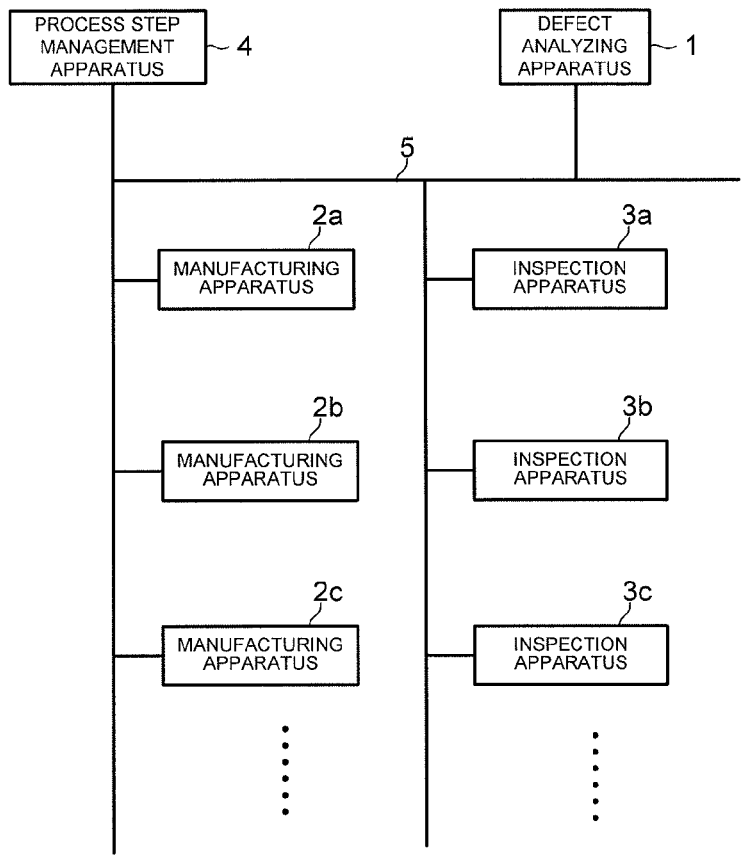
FIG. 1 is a constitutional diagram of a defect analyzing system according to a first embodiment.

FIG. 1 is a diagram illustrating an example of a constitution of a defect analyzing system according to a first embodiment. The defect analyzing system according to the first embodiment includes a defect analyzing apparatus 1, a plurality of manufacturing apparatuses 2a, 2b, 2c . . . (hereinafter, referred to as a manufacturing apparatus 2), a plurality of inspection apparatuses 3a, 3b, 3c . . . (hereinafter, referred to as an inspection apparatus 3), a process step management apparatus 4, and a network 5 such as a LAN (Local Area Network) connecting the above. The network 5 may be either wired or wireless.

The process step management apparatus 4 transmits/receives information (data) to/from the manufacturing apparatus 2, the inspection apparatus 3 and so on to/from each other, thereby to manage a manufacturing process step of a semiconductor device. More specifically, the process management apparatus 4 instructs the manufacturing apparatus 2 and the inspection apparatus 3 to perform a processing and an inspection of a semiconductor substrate (hereinafter, referred to as a wafer), based on manufacturing process steps (hereinafter, referred to as a process step flow) of the semiconductor device, the manufacturing process steps being registered in advance and different per model. As a method of communication, there can be used an SECS (SEMI Equipment Communications Standard) or a GEM 300 (Generic Equipment Model for 300 mm wafer) prescribed by an SEMI (Semiconductor Equipment and Materials Institute), for example.

The manufacturing apparatus 2 is a manufacturing apparatus which manufactures a semiconductor device by processing a wafer. As the manufacturing apparatus 2, there are an implant apparatus, a cleaning apparatus, a coater, an exposure apparatus (a stepper), a developer, a PVD (Physical Vapor Deposition) apparatus, a CVD (Chemical Vapor Deposition) apparatus, a CMP (Chemical Mechanical Polishing) apparatus, a dicing apparatus, a bonding apparatus, and so on, for example.

The manufacturing apparatus 2 transmits a processing condition (a gas pressure in a chamber, a gas flow amount, a heater temperature or the like, in a wafer processing, for example) of the wafer having been processed to the process step management apparatus 4 with a Lot ID (hereinafter, referred to as a LID), a wafer ID (hereinafter, referred to as a WID), a making time (a time stamp), an ID of a person in charge, a model name, a process step number, and so on.

The inspection apparatus 3 is an apparatus which inspects a semiconductor device formed on a wafer. As the inspection apparatus, there are a defect detection apparatus, a waveform measuring apparatus, a film thickness measuring apparatus, and so on, for example. The defect detection apparatus detects a defect of the semiconductor device formed on the wafer. The defect detection apparatus takes an image of the semiconductor device formed on a predetermined position on the wafer and compares the image having been taken with a sample image of a good semiconductor device, thereby to detect a defect.

Figure 2:
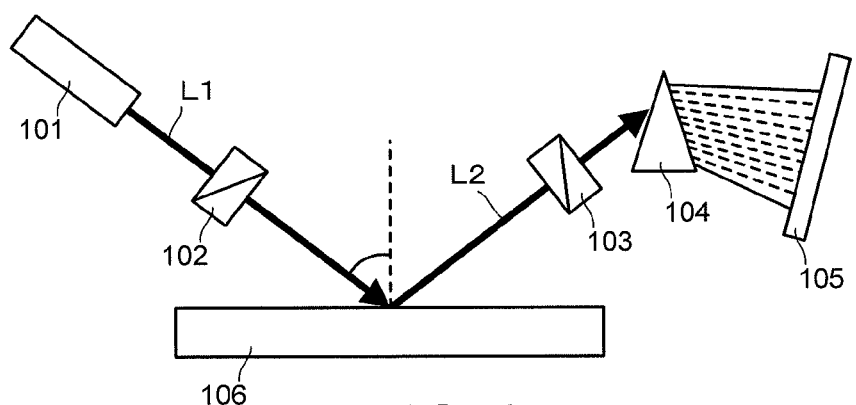
FIG. 2 is a schematic diagram of ellipsometry.

The waveform measuring apparatus acquires waveforms (spectra) of a reflection wave and an interference wave by an electron beam or an ellipsometry in a region which includes the defect detected by the defect detection apparatus. FIG. 2 is a schematic diagram of the ellipsometry. As illustrated in FIG. 2, the ellipsometry usually includes a light source 101, a polarizer 102, an analyzer 103, a prism 104, a detector 105, and so on. The light source 101 houses a collimator lens making an emitted light be a collimator light. A polarization surface of the polarizer 102 and a polarization surface of the analyzer 103 are disposed in a state of being displaced by 90 degrees, that is, in a state of being orthogonal.

An incident light L1 emitted from the light source 101 becomes a linearly polarized light by the polarizer 102 and is irradiated to an object 106 to be measured. A specific polarization component among a reflected light L2 reflected in a surface of the object 106 to be measured or in a region which includes the surface of the object 106 to be measured penetrates through the analyzer 103. The light having penetrated through the analyzer 103 is spectrumed per frequency band by the prism 104 and is detected by the detector 105, thereby to be recognized as a waveform (spectrum).

The film thickness measuring apparatus is used in a QC (Quality Control) performed periodically, and measures a thickness of a film deposited by a PVD apparatus or a CVD, or an etch rate of an etching apparatus.

The inspection apparatus 3 transmits an inspection result of the semiconductor device formed on the wafer, that is, a position and a size of the defect detected by the defect inspection apparatus, the film thickness and the etch rate measured by the thickness measuring apparatus, and the waveform measured by the waveform measuring apparatus and information (an incident wavelength, an incident angle, an angle of deviation, and so on) such as an acquisition condition of the waveform or the like, to the defect analyzing apparatus 1 with information such as an LID, a WID, a measurement time (time stamp), an ID of the person in charge, a model name, and a process step number, respectively.

The etch rate is measured by using a wafer for etch rate measurement on which a desired film is deposited. In other words, an initial film thickness $T_{in}$ of a film deposited on a wafer and a remaining film thickness $T_{af}$ after etching are measured by the film thickness measuring apparatus, and an absolute value of a difference between the initial film thickness $T_{in}$ and the remaining film thickness $T_{af}$ is divided by an etching time (60 s, for example), so that an etch rate is calculated. The calculated etch rate is transmitted to the defect analyzing apparatus 1 as described above.

Though in the above explanation the inspection of the defect and the acquisition of the waveform are performed by different inspection apparatuses 3, the inspection of the defect and the acquisition of the waveform can be performed by the same inspection apparatus 3. In the following explanation, the waveform acquired by the inspection device 3 is referred to as a "real waveform", to be distinguished from a waveform acquired by an optical simulation described later.

The defect analyzing apparatus 1 is a shape, process and optical simulator of a semiconductor device. The defect analyzing apparatus 1 receives the inspection result transmitted from the inspection apparatus 3 and the process step flow transmitted from the process step management apparatus 4, and analyzes the defect detected by the inspection apparatus 3. More specifically, a generation process of a defect is simulated based on the inspection result transmitted from the inspection apparatus 3 and the process step flow transmitted from the process step management apparatus 4, thereby to specify the manufacturing process step causing the defect.

It is also possible that the above-described process step flow is stored in the defect analyzing apparatus 1 in advance as a default and that the stored process step flow is used. In such a case, a film thickness, an etch rate and so on stored in the defect analyzing apparatus 1 are to be replaced by a film thickness, an etch rate and so on acquired from the manufacturing apparatus 2 as necessary.

Figure 3:
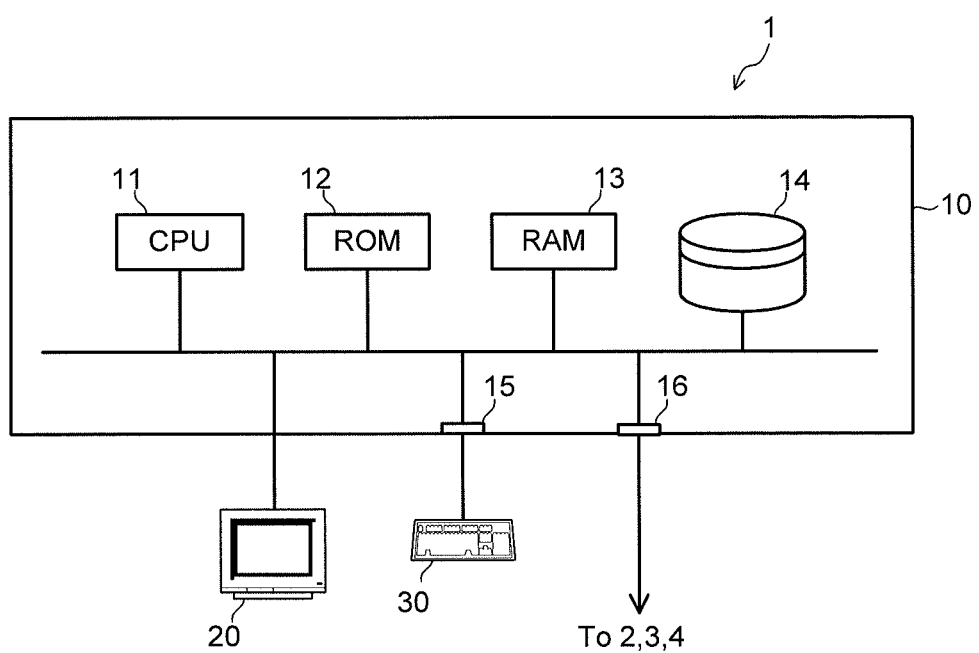
FIG. 3 is a constitutional diagram of a defect analyzing apparatus according to the first embodiment.

FIG. 3 is a diagram illustrating an example of a constitution of the defect analyzing apparatus 1. The defect analyzing apparatus 1 includes a computer main body 10, and a monitor 20 and an input device 30 such as a key board or a mouse which are connected to the computer main body 10.

The computer main body 10 includes a CPU 11, a ROM 12, a RAM 13, an HDD 14, a user I/F 15 and an I/F 16. The CPU (Central Processing Unit) 11 controls the entire defect analyzing apparatus 1. The ROM (Read Only Memory) 12 stores an operational code of the CPU 11. The RAM (Random Access Memory) 13 is a working area used at a time of an operation of the CPU 11. In the HDD (Hard Disk Drive) 14, a program for simulation, the inspection result of the semiconductor device by the inspection apparatus 3, and so on are stored. The user I/F 15 is an interface to accept input information from the input device 30. The I/F 16 is an interface for performing transmission/reception of data to/from the manufacturing apparatus 2, the inspection apparatus 3, and the process management apparatus 4.

Figure 4:
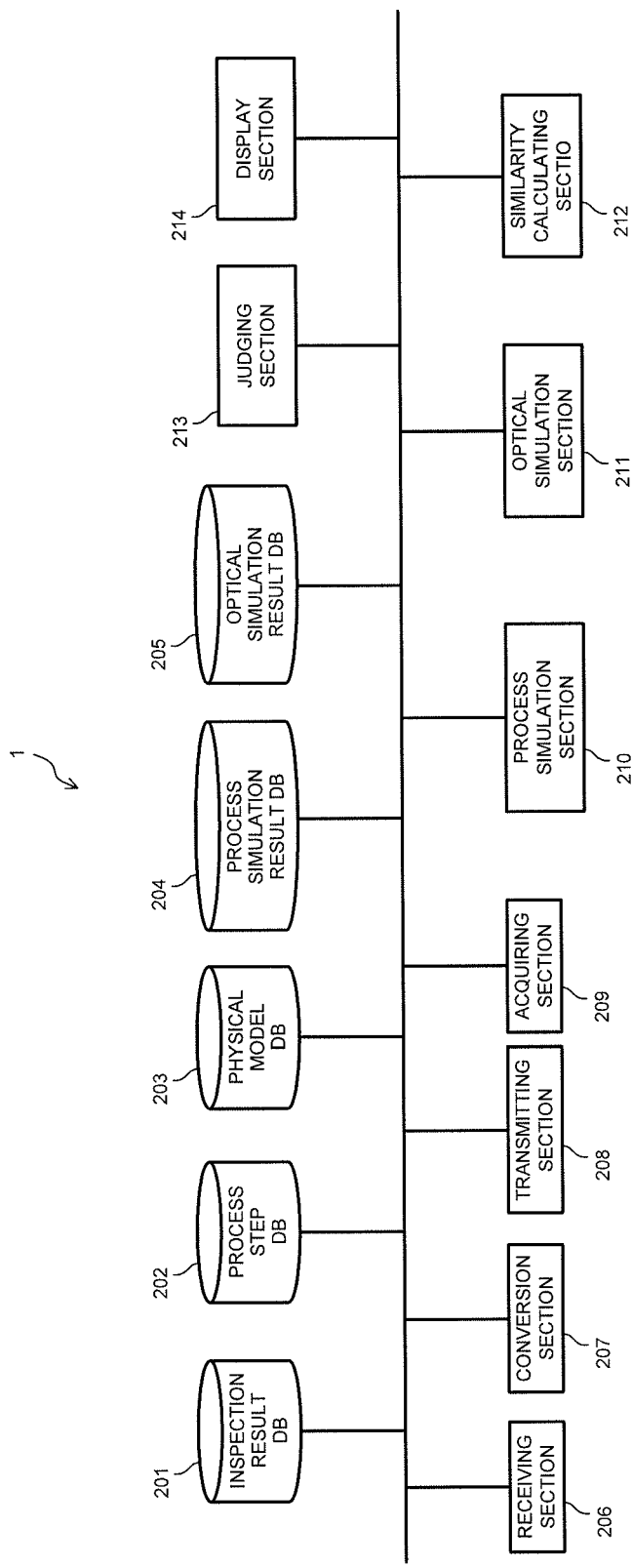
FIG. 4 is a functional diagram of the defect analyzing apparatus according to the first embodiment.

FIG. 4 is a diagram illustrating an example of a function of the defect analyzing apparatus 1 according to the first embodiment. The defect analyzing apparatus 1 includes an inspection result DB 201, a process step flow DB 202, a physical model DB 203, a process simulation result DB 204, an optical simulation result DB 205, a receiving section 206, a conversion section 207, a transmitting section 208, an acquiring section 209, a process simulation section 210, an optical simulation section 211, a similarity calculating section 212, a judging section 213, and a display section 214. The functions indicated in FIG. 4 are realized as a result that the CPU 11 performs the program stored in the HDD 14 using the RAM 13 as the working area.

In the inspection result DB 201, there is stored the inspection result of the semiconductor device transmitted from the inspection apparatus 3, more specifically, the position and the size of the defect detected in the inspection apparatus 3, the film thickness and the etch rate in the QC, and the real waveform and so on, with the LID, the WID, and the process step number. In the process step flow DB 202, the process step flow transmitted from the process step management apparatus 4 is stored with the LID. The inspection result and the process step flow, after converted into formats processable by the defect analyzing apparatus 1 in the conversion section 207, are stored into the inspection result DB 201 and the process step flow DB 202.

FIG. 5 is a diagram illustrating an example of the process step flow stored in the process step flow DB 202. In the process step flow, the manufacturing process steps of the semiconductor device are aligned in chronological order, and the process step numbers, the process step names and processing contents of the respective process steps are written in a corresponding manner. The LID and the model name are written in each process step flow. Therefore, the process step of a lot corresponding to the LID and the model name as well as the content in each process step can be known from the process step flow. For example, in the example illustrated in FIG. 5, it is understood that in a process step 1 a sacrifice oxide film is formed and that its film thickness is 9 to 11 nm.

The physical model DB 203 stores a variety of physical models necessary for a shape simulation in which etching, deposition (film deposition) and lithography process steps are simulated, for a process simulation in which an oxidation and an impurity diffusion process step are simulated, and for an optical simulation for acquiring a waveform by an ellipsometry or the like. In the following explanation, it is presumed that the process simulation includes the shape simulation.

Among models used in the process simulation of the semiconductor device, there is a Monte Carlo method, for example. The Monte Carlo method is a physical model to simulate injection of an impurity (a dopant) in an implantation process step.

The physical model used in the process simulation of the semiconductor device is generally solved by a finite volume method or a finite difference method. In the finite volume method, an object to be analyzed is finely divided into a plurality of meshes (elements) and a transient analysis is performed in a manner to fulfill a law of conservation of mass, a law of conservation of momentum and a law of conservation of energy per finely divided mesh, while in the finite difference method, a differential of a differential equation which gives the law of conservation of mass, the law of conservation of momentum and the law of conservation of energy is approximated by a divided difference thereby to solve the differential equation.

In order to perform the optical simulation, the physical model DB 203 stores a physical coefficient such as a reflectivity or a penetrable rate of each material to be used in the semiconductor device, a calculation expression to calculate an interference of the light, and so on.

Process simulators of semiconductor devices which incorporate the above-described physical model are commercialized by Synopsys Corporation, Silvaco Corporation and so on. As the defect analyzing apparatus 1 according to the first embodiment, those commercialized process simulators can be used.

The process simulation result DB 204 stores a result (information of a shape, a material and so on) of the process simulation in a later-described process simulation section 210.

The optical simulation result DB 205 stores a result (information of a waveform) of the optical simulation in a later-described optical simulation section 211.

The receiving section 206 receives the inspection result transmitted from the inspection apparatus 3 and the process step flow transmitted from the process step management apparatus 4.

The conversion section 207, after converting the inspection result transmitted from the inspection apparatus 3 and the process step flow transmitted from the process step management apparatus 4, the inspection result and the process step flow being received by the receiving section 206, into a format processable by the defect analyzing apparatus 1, stores into the inspection result DB 201 and the process step flow DB 202, respectively.

The transmitting section 208 transmits the LID stored with the inspection result in the inspection result DB 201 to the process step management apparatus 4. The process step management apparatus 4, receiving the LID transmitted from the defect analyzing apparatus 1, transmits the process step flow corresponding to the received LID to the defect analyzing apparatus 1.

The acquiring section 209 acquires the inspection result from the inspection result DB 201. The acquiring section 209 acquires the process step flow having the same LID as that of the acquired inspection result from the process step flow DB 202.

The process simulation section 210 simulates a generation process of a defect based on an inspection result and a process step flow acquired from the acquiring section 209, thereby to specify a manufacturing process step having caused the defect.

Figure 6:
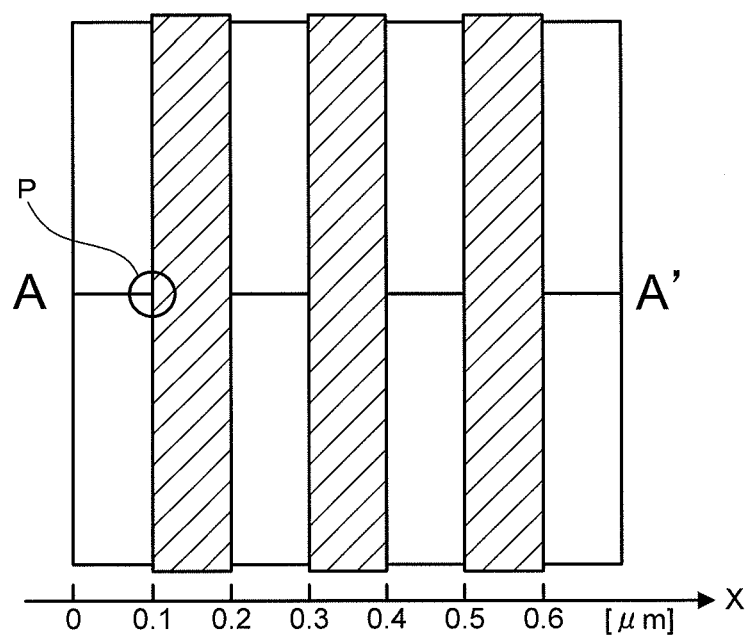
FIG. 6 is a schematic diagram of a defect detected by an inspection apparatus.
Figure 7A:
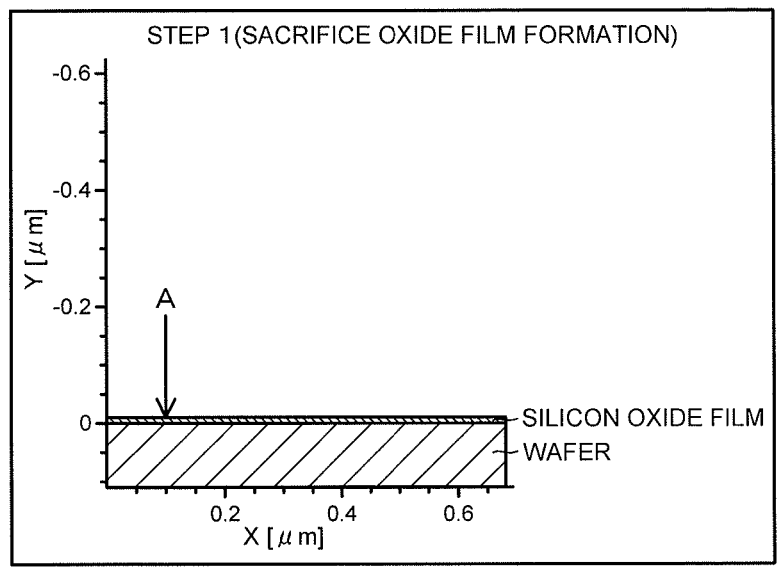
FIGS. 7A to 7E are explanatory diagrams of process simulations.
Figure 7B:
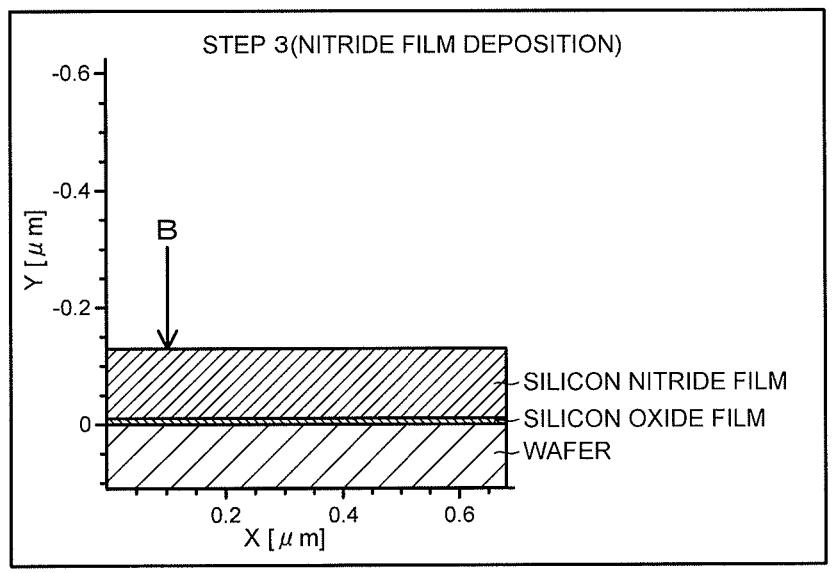
Figure 7C:
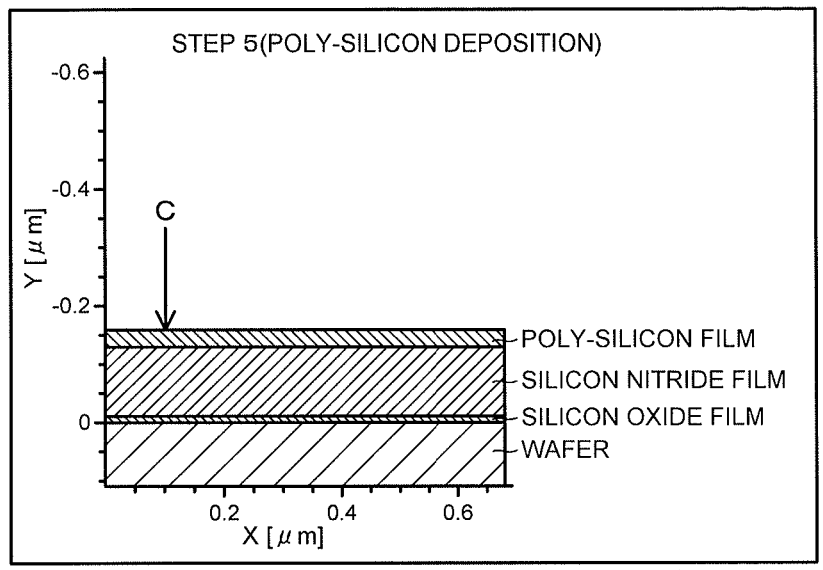
Figure 7D:
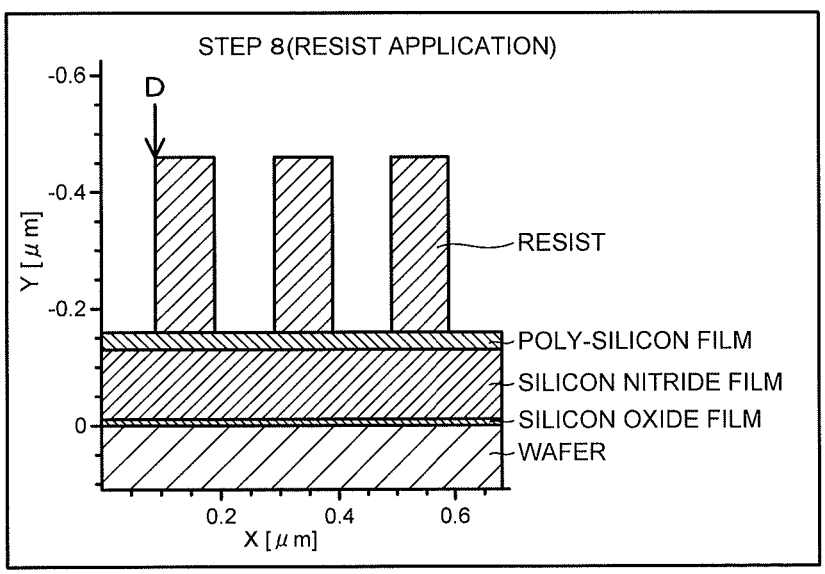
Figure 7E:
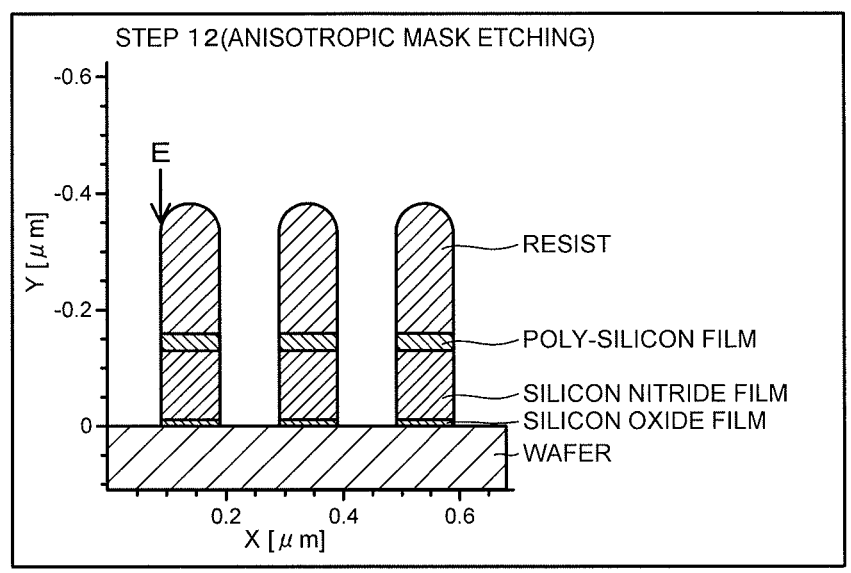

FIG. 6 is a schematic diagram of a defect P detected by the inspection apparatus 3 (an defect detection apparatus). In the first embodiment, it is assumed that the defect P (a foreign object) is detected in a process step 15 (a defect inspection 2) of the process step flow illustrated in FIG. 5. Hereinafter, an operation of the process simulation section 210 will be explained with reference to FIG. 6.

(Process Simulation)

The process simulation section 210 recognizes that the defect P illustrated in FIG. 6 is 0.1 μm (x axis) in position and 30 nm in size (diameter) from the inspection result acquired by the acquiring section 209. Next, the process simulation section 210 replaces the film thickness and the etch rate in film forming and etching process steps in the acquired process step flow with the film thickness and the etch rate in the QC transmitted from the inspection apparatus 3, thereby to generate a process step flow for simulation. Thereby, it becomes possible to perform a simulation by using a film thickness of actual deposition, leading to improvement of simulation accuracy. With regard to data of the film thickness and the etch rate to be used in the above-described replacement, data measured in the same model and data closest in terms of time is to be used. The time can be recognized from a time stamp transmitted with the data.

The process simulation section 210 simulates the generation process of the defect based on the recognized position and size of the defect and the generated process step flow for simulation. On this occasion, the process simulation section 210 hypothetically generates a nucleus to be a base of the defect at a position (position at 0.1 μm on the x axis) corresponding to the recognized position of the defect in each process step except the inspection process step, thereby to simulate the generation process of the defect.

FIGS. 7A to 7E are diagrams illustrating process steps to hypothetically generate the nucleuses. FIGS. 7A to 7E illustrate cases in which the nucleuses are each generated in a process step 1 (sacrifice oxide film formation), a process step 3 (nitride film deposition), a process step 5 (polysilicon deposition), a process step 8 (resist coating) and a process step 12 (anisotropic etching).

The process simulation section 210, after hypothetically generating the nucleus to be the base of the defect at positions A to E corresponding to the recognized position of the defect illustrated in FIGS. 7A to 7E in the process step 1, the process step 3, the process step 5, the process step 8, and the process step 12, simulates the generation process of the defect in each position. Though a variety of materials can be set as a material of the nucleus to be generated in each process step, usually the nucleus as above often occurs in a deposition process step of a film. Thus, in the first embodiment, three kinds of materials, i.e., silicon oxide, silicon nitride and poly-silicon, are dealt with, but it is a matter of course that a nucleus of a material other than the above-described materials ($SiO_2$, $Si_3N_4$, Poly-Si) may be generated.

Figure 8:
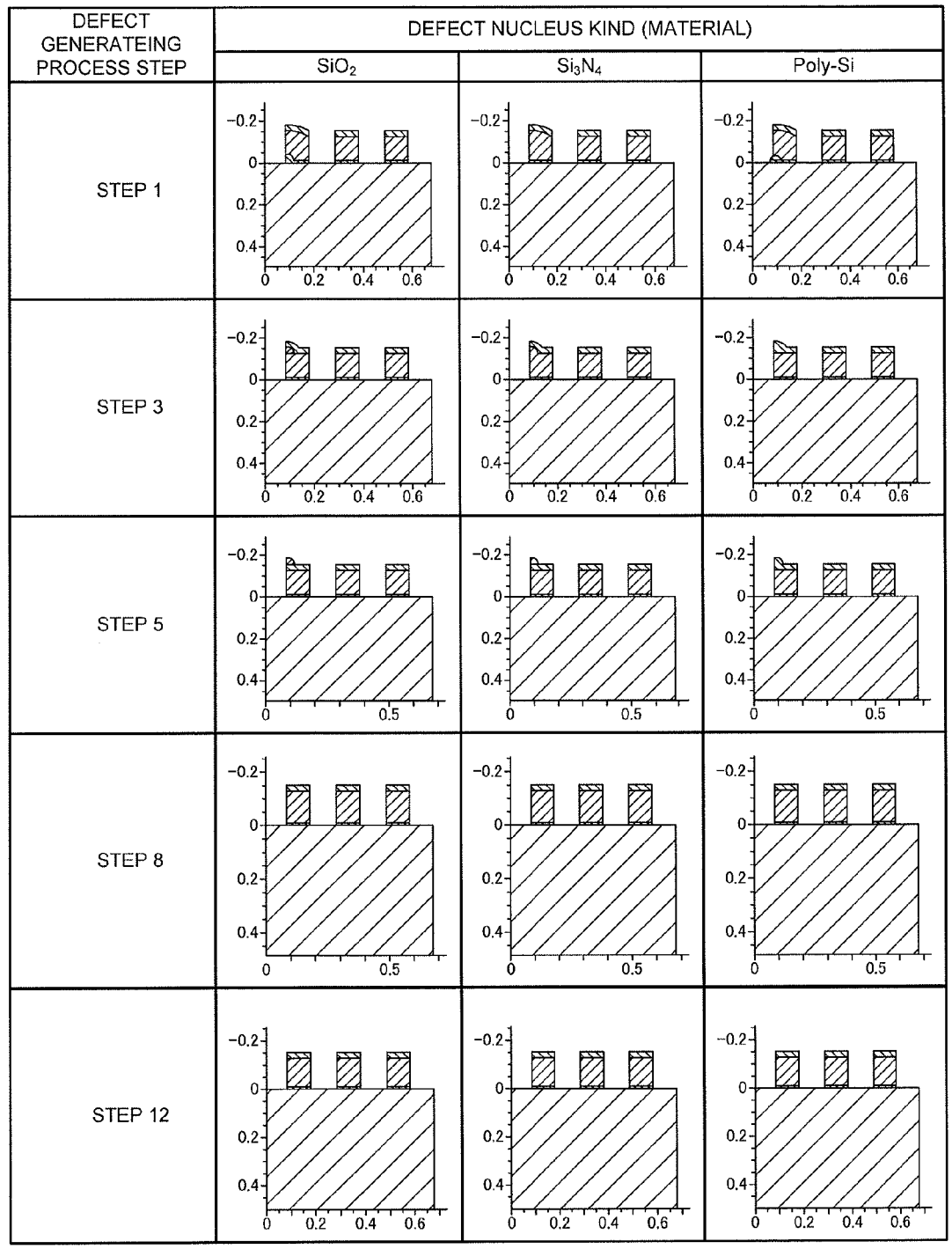
FIG. 8 is a table exemplifying patterns of the simulations.

FIG. 8 is a table which exemplifies patterns of the simulation by the process simulation section 210. In FIG. 8, process steps to generate the nucleus are aligned in sequence of process steps in a vertical direction, while materials of the nucleuses to be generated in the respective process steps are aligned in sequence of silicon oxide (SiO$_2$), silicon nitride (Si$_3$N$_4$), and poly-silicon (Poly-Si) in a horizontal direction.

As described above, if the defect (the foreign object) is detected in the process step 15 (the defect inspection 2) in the process step flow illustrated in FIG. 5, it is necessary to generate nucleuses whose material are silicon oxide, silicon nitride and poly-silicon in the process step 1, the process step 3, the process step 5, the process step 7 and the process step 12, respectively. Therefore, the process simulation section 210, as illustrated in FIG. 8, performs 15 types of simulations in which nucleuses of three kinds of materials are generated in the above-described 5 process steps, respectively, and 15 types of simulation results thereof are stored into the process simulation result DB 204.

Figure 9A:
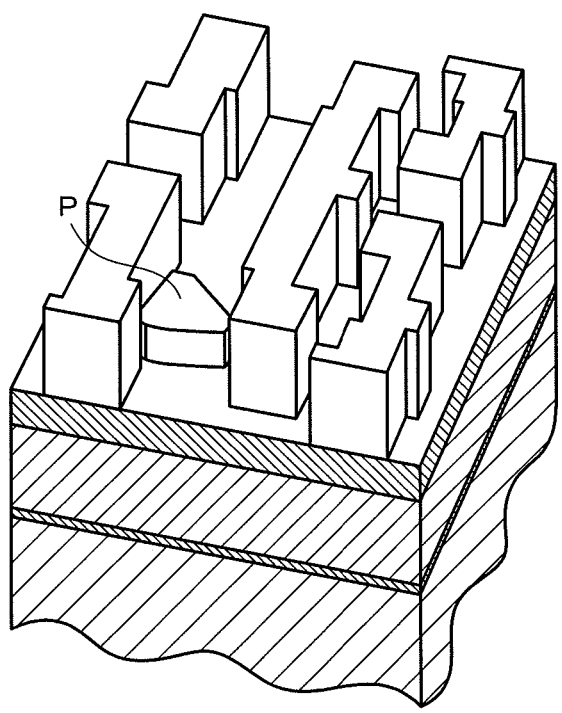
FIGS. 9A and 9B are diagrams illustrating examples of virtual defect calculated by process simulation based on detected defects.
Figure 9B:
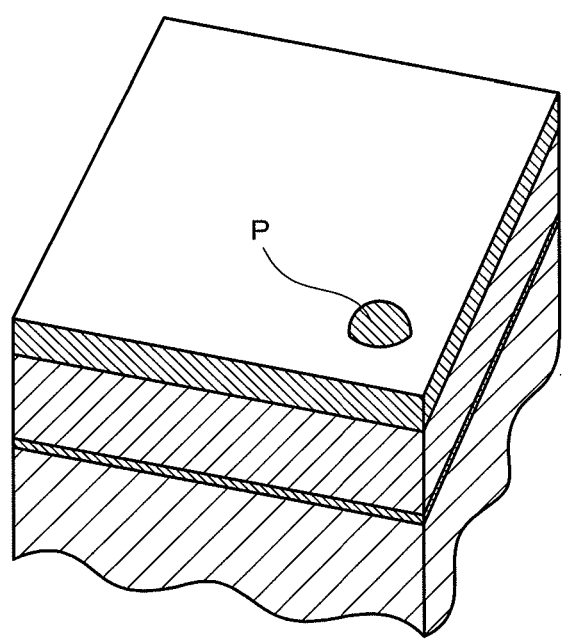

A size and a shape of the nucleus to be generated are determined based on a shape and a size of a detected defect. FIG. 9A and FIG. 9B are diagrams illustrating examples of virtual defect calculated by process simulation based on detected defects. FIG. 9A illustrates a case in which the shape of the defect has a geometrical feature, while FIG. 9B illustrates a case in which the shape of the defect does not have a geometrical feature. As illustrated in FIG. 9A, if the shape of the detected defect has the geometrical feature, the process simulation section 210 makes films (a silicon oxide film, a silicon nitride film, a poly-silicon film) deposited in a manner that the film has a shape the same as that of the defect, at a position corresponding to an acquired position of the defect.

As illustrated in FIG. 9B, if the shape of the detected defect does not have the geometrical feature, the process simulation section 210, after generating a nucleus of a rectangle (in a case of a two-dimensional simulation) or of a cube (in a case of a three-dimensional simulation) which is smaller than the detected defect at a position corresponding to a position of an acquired position of the defect, performs an isotropic deposition which is material-selective by centering on the nucleus. A size of the nucleus is to be smaller than a size of the defect detected in the inspection apparatus 3, and the size of the nucleus is made smaller as process steps are earlier than the process step in which the defect is found.

As illustrated in FIG. 9B, if the shape of the detected defect does not have the geometrical feature, after a nucleus of a material A which is a material other than silicon oxide, silicon nitride and poly-silicon is generated, an isotropic deposition which is material-selective may be performed, and thereafter, the material A may be replaced by silicon oxide, silicon nitride or poly-silicon. By performing a simulation by such a procedure, a simulation procedure can be made simpler.

(Optical Simulation)

The optical simulation section 211 simulates an optical property of a pattern of each simulation generated by the process simulation section 210 by using a reflectivity (n), refractive index (k) of each film kind and an optical system (an incident wavelength, an incident angle, an angle of deviation, or the like) of the ellipsometry as an input value, so that a waveform is acquired. The optical simulation section 211 performs a simulation on each simulation result simulated by the process simulation section 210 and stored in the process simulation result DB 204, under a condition the same as an acquisition condition of a waveform acquired by the acquiring section 209 in the inspection apparatus 3, and then generates a waveform corresponding to each simulation result, and stores into the optical simulation result DB 205.

Figure 10A:
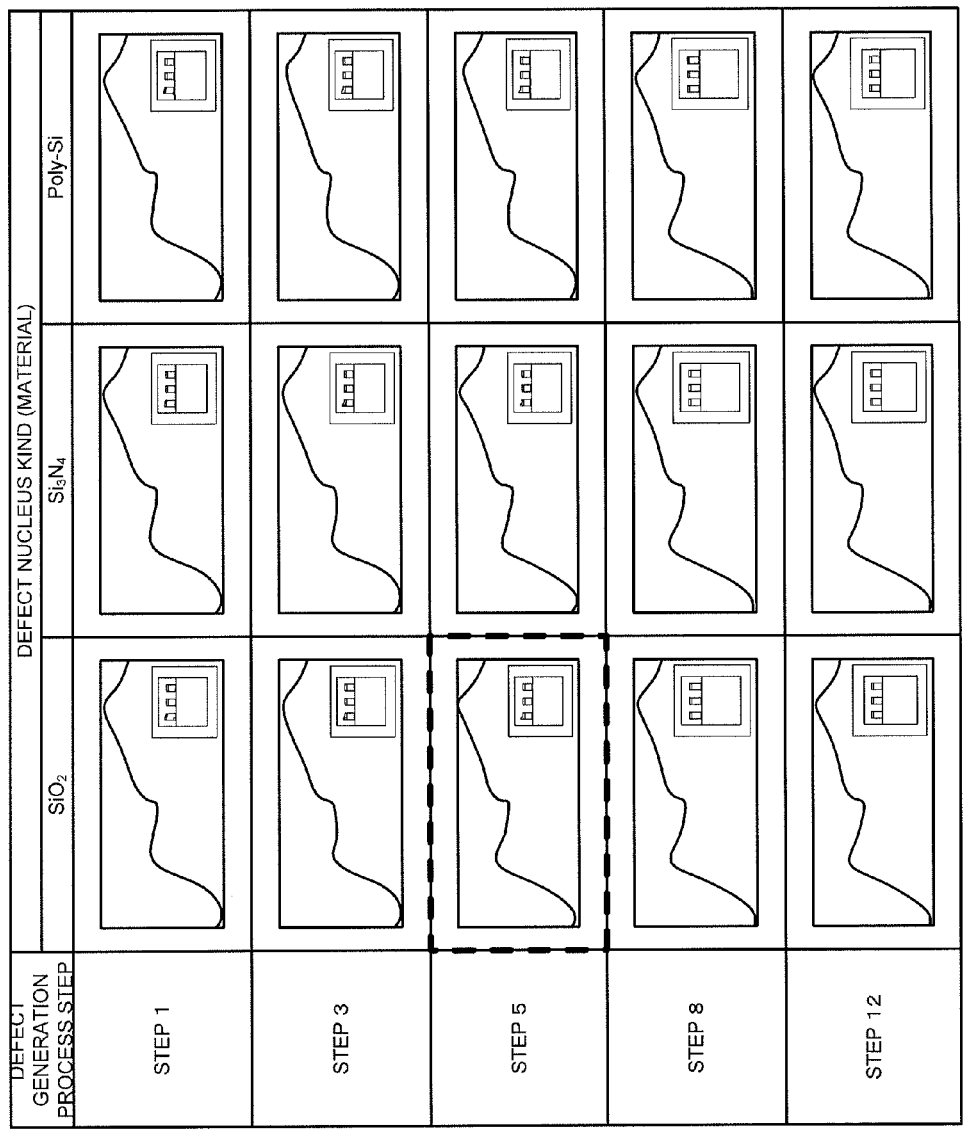
FIGS. 10A and 10B are tables illustrating results of optical simulations calculated based on the virtual defect of FIG. 9.
Figure 10B:
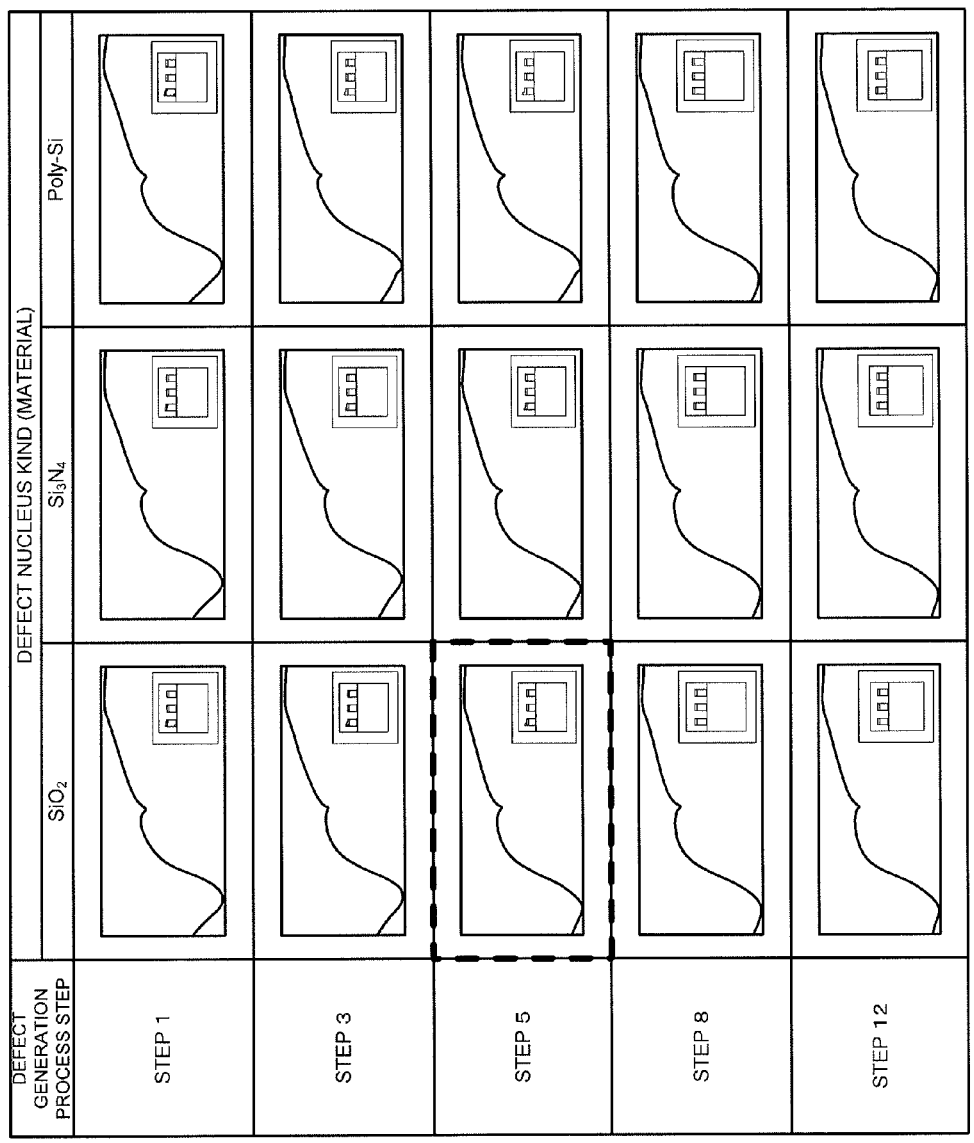

FIG. 10A and FIG. 10B are tables illustrating the simulation results acquired by the simulation in the optical simulation section 211 based on the virtual defect of FIG. 9. FIG. 10A and FIG. 10B illustrate waveforms of $\alpha$ and $\beta$ of a normalized Fourier coefficient, respectively. The $\alpha$ and $\beta$ are represented by the following formula (1) and formula (2), respectively.

$$\alpha = (\cos 2P - \cos 2\Psi)/(1 - \cos 2P \cos 2\Psi) \quad (1)$$

$$\beta = (\sin 2\Psi \cos \Delta \sin 2P)/(1 - \cos 2P \cos 2\Psi) \quad (2)$$

Here, $\Delta$, $\Psi$, P are used to represent the following.
$\Delta$: a phase difference of a reflected light (L2 of FIG. 2) in relation to an incident light (L1 of FIG. 2)
$\Psi$: an amplitude ratio of the reflected light (L2 of FIG. 2) in relation to the incident light (L1 of FIG. 2)
P: an angle of a polarizer (102 of FIG. 2) in relation to the incident light (L1 of FIG. 2)

Since the optical simulation is performed on each of the 15 types of simulation results simulated by the process simulation section 210, there are also acquired 15 types of results of the optical simulations (as illustrated in FIG. 10A and FIG. 10B, 15 types of simulation results are acquired for each of $\alpha$ and $\beta$).

The similarity calculating section 212 acquires the real waveform of the LID on which a simulation is performed by the optical simulation section 211, from the inspection result DB 201. The judging section 213 calculates a similarity degree between the waveform stored in the optical simulation result DB 205 and the real waveform. For such calculation of the similarity degree, there can be used a variety of methods, for example, a method of selecting a condition where a square sum of a difference between waveforms of each reflected wave acquired in the simulation becomes the minimum while using an actual measured waveform as a reference, a method of Fourier-transforming an actual measured waveform and a simulation waveform to compare spectra, and so on.

The judging section 213 judges that the similarity degree exceeding a threshold value stored in advance, among the similarity degrees calculated by the similarity calculating section 212, is a cause of the defect.

The display section 214 acquires the optical simulation result which has been judged to be the cause of the defect by the judging section 213 and the process simulation result corresponding to the waveform thereof from the optical simulation result DB 205 and the process simulation result DB 204, respectively, and displays in the monitor 20.

(Operation of Defect Analyzing System)

Figure 11:
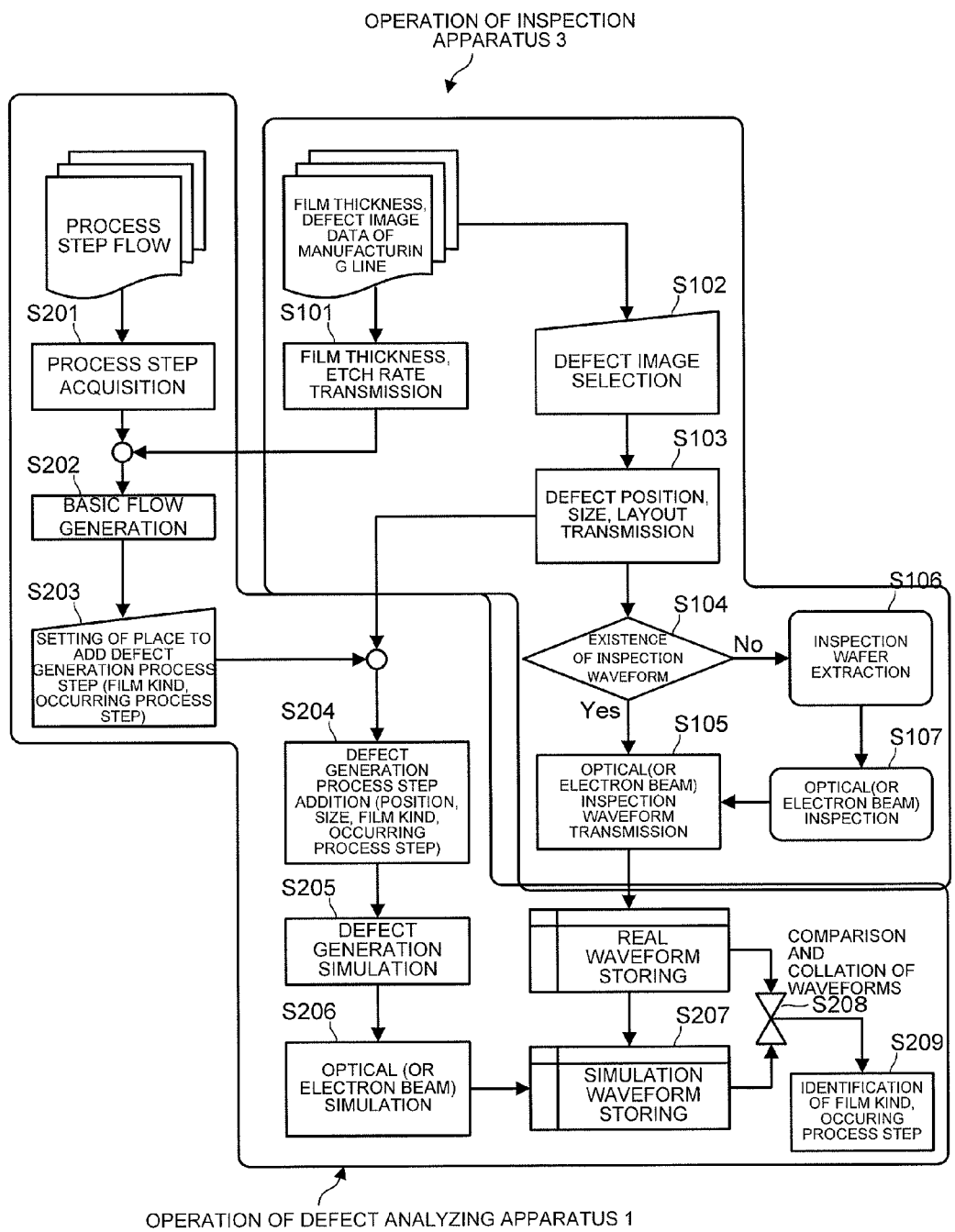
FIG. 11 is a flowchart illustrating an example of an operation of the defect analyzing system according to the first embodiment.

FIG. 11 is a flowchart illustrating an example of an operation of the defect analyzing system. Hereinafter, the operation of the defect analyzing system is explained with reference to FIG. 11. In explanation, the operation is divided into an operation (step S101 to step S108) of the inspection apparatus 3 and an operation (step S201 to step S210) of the defect analyzing apparatus 1.

First, the operation of the inspection apparatus 3 is explained.

(Step S101)

The inspection apparatus 3 transmits information such as a film thickness, an etch rate or the like acquired in a QC performed periodically to the defect analyzing apparatus 1.

(Step S102, Step S103)

The inspection apparatus 3 performs an inspection of a semiconductor device formed on a wafer, and after detecting a defect of the semiconductor device formed on the wafer, the inspection apparatus 3 extracts information such as a position and a size of the defect and transmits to the defect analyzing apparatus 1.

(Step S104 to Step S107)

If the defect is detected, the inspection apparatus 3 judges whether a waveform (a spectrum) which includes the defect has been acquired. If the waveform has been already acquired, that waveform (the real waveform) is transmitted to the defect analyzing apparatus 1. If the waveform has not been acquired, that waveform (the real waveform) is acquired and transmitted to the defect analyzing apparatus 1.

Next, the operation of the defect analyzing apparatus 1 is explained.

(Step S201)

The acquiring section 209 acquires a process step flow corresponding to an inspection result transmitted from the inspection apparatus 3, from the process step flow DB 202.

(Step S202 to Step S204)

The process simulation section 210 replaces a film thickness and an etch rate of a recipe of film forming and etching process steps in the acquired process step flow with a film thickness and an etch rate transmitted from the inspection apparatus 3 and generates a process step flow for simulation. Next, the process simulation section 210 generates a plurality of process step flows for simulation to which process steps of defect generation are added based on the recognized position and size of the defect.

(Step S205)

The process simulation section 210 performs a simulation of defect generation on each of the generated plural process step flows for simulation.

(Step S206, S207)

The optical simulation section 211 generates a waveform simulating an optical property of each simulation result generated by the process simulation section 210, and stores into the optical simulation result DB 205.

(Step S208, S209)

The similarity degree calculating section 212 compares the waveform made by the simulation in the optical simulation section 211 with the real waveform, thereby to calculate a similarity degree of the respective simulation results. The judging section 213 judges the similarity degree exceeding a threshold value stored in advance, among the calculated similarity degrees, to be the cause of the defect.

The display section 214 acquires an optical simulation result judged to be the cause of the defect by the judging section 213 and the process simulation result corresponding to the waveform thereof from the optical simulation result DB 205 and the process simulation result DB 204, respectively, and displays in the monitor 20.

As described above, the defect analyzing apparatus 1 according to the first embodiment performs the process simulation to simulate a plurality of processes of defect generation with different generation conditions, based on the position and the size of the defect and the process step flow, of the semiconductor device. Next, the optical simulation is further performed on the result of the process simulation, and, after the waveform is generated, the generated waveform is compared with the real waveform of the defect and the similarity degree is calculated, and one whose similarity degree exceeds the threshold value stored in advance is judged to be the cause of the defect.

Therefore, even in a case in which there is an inspection process stepper several process steps to several ten process steps, it is possible to effectively specify in which manufacturing process step a defect or a factor to cause a defect has occurred.

Other Embodiments

The present invention is not limited to the above-described embodiment and may be embodied while modifying components without departing from the scope thereof in an execution phase. For example, it is possible to constitute so that a user can change a process step flow accordingly by using the input device 30. FIG. 12 to FIG. 15 are views illustrating examples of an input screen for process step flow change, the input screen being displayed in the monitor 20.

Figure 12:
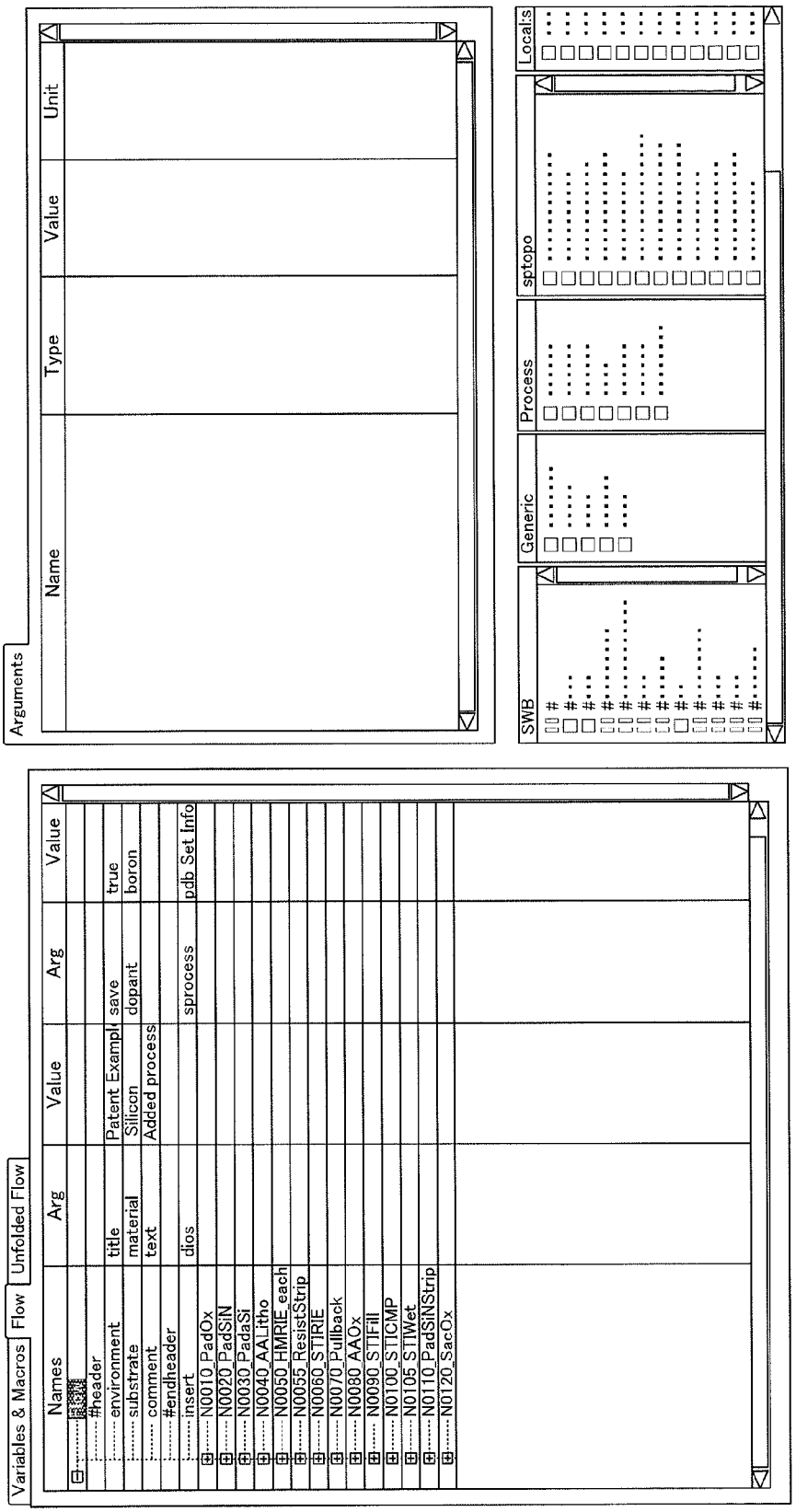

FIG. 12 is the example of the screen in which a process step for simulation is inputted according to the process step flow. In the example illustrated in FIG. 12, the process step flow can be created by inputting a name and a content of each process step flow into a left column in an order of the process step flow.

Figure 13:
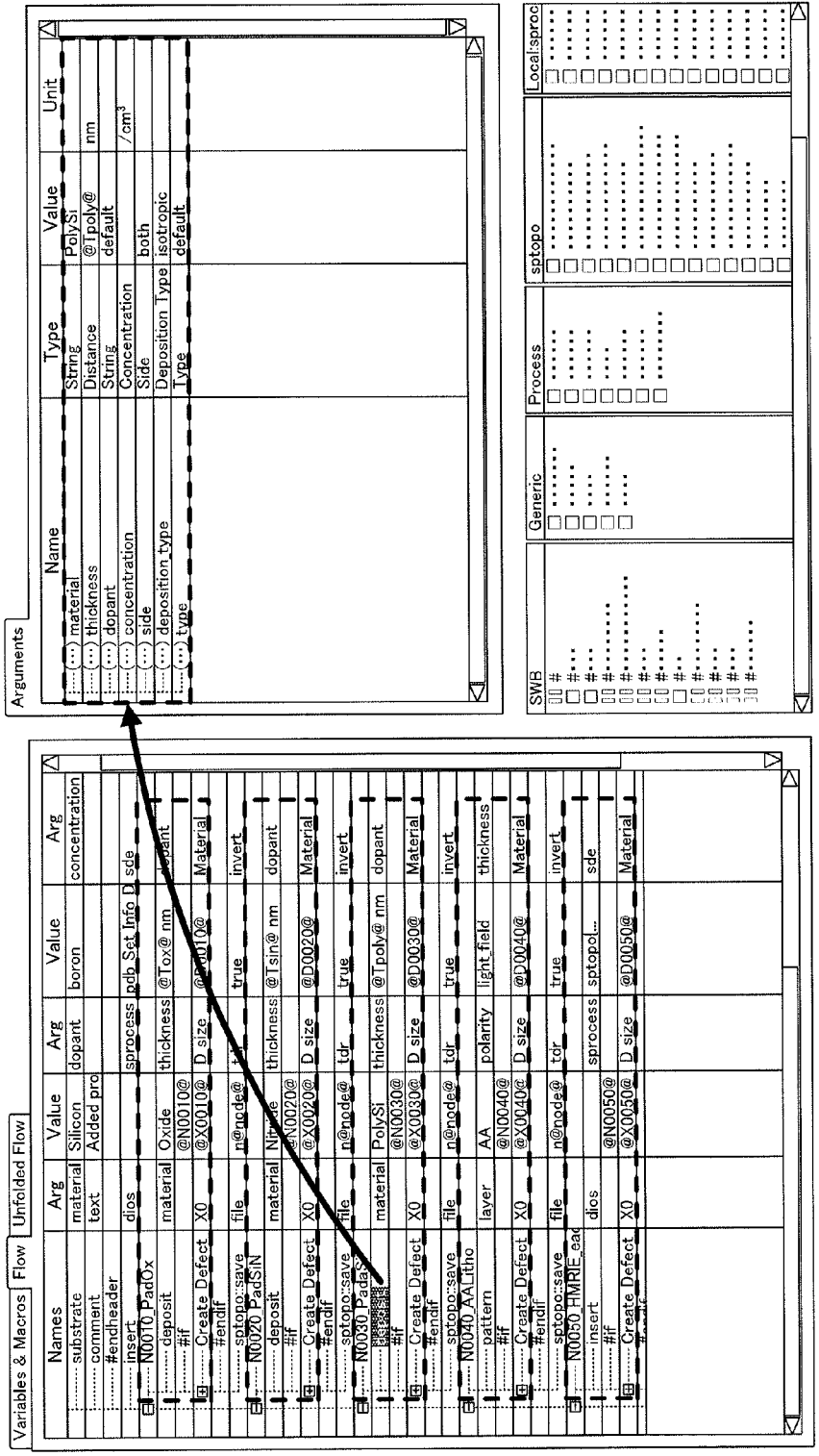

FIG. 13 is the example of the screen in which a detailed condition of each process step created in FIG. 12 is inputted. Within a dotted line frame in an upper right side of FIG. 13 there are presented condition details of the process step 5 (poly-silicon deposition) of FIG. 5. Within a dotted line frame in the left of the screen, there are presented simulation codes for generating defects having desired diameters at desired positions. In the example of FIG. 13, when a value of a variable (@ to @) written directly after #if is "1", defect generation is performed.

Figure 14:
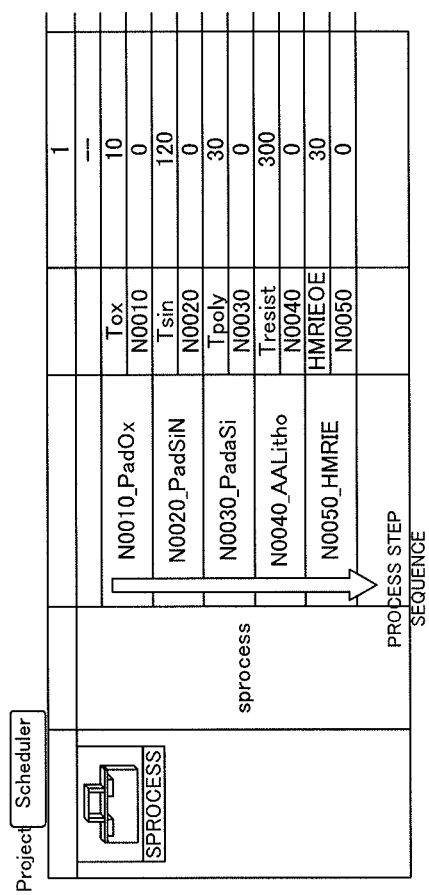

FIG. 14 is the example of the screen in which a parameter (a film thickness, an etch rate, a process time and so on) of each process step presented in FIG. 13 is inputted.

FIG. 15 is the example of the screen in which a position, a size and a material of the defect is inputted. The example illustrated in FIG. 15 is an input example of a case in which a defect of 0.03 µm in diameter (D size) is generated at a position (X0) of 0.1 µm. In FIG. 15, as the material of the defect, silicon oxide (oxide), silicon nitride (nitride) and poly-silicon (PolySi) are designated. Parameters N0010 to N0050 each have a value "1" or "0", and if the value is "1", the defect presented in the dotted line frame is generated in that process.

By constitution so that various of parameters of the process simulation can be designated by the user as above, a variety of cases of defect generation can be simulated, and an experience of the user can be incorporated in specification of a defect or a factor to cause a defect. As a result, it can be expected that a defect or a factor to cause a defect can be specified more effectively.

If a defect is detected in an arbitrary inspection process step, it is highly possible that the defect is generated between a previous inspection and the present inspection. Thus, as acquisition of the process step flow in the acquiring section 209, only a portion from a process step in which a defect is detected to a previous inspection process step may be acquired. By constituting as above, it is possible to reduce a load of a simulation processing in the process simulation section 210 and the optical simulation section 211.

While certain embodiments have been described, these embodiments have been presented by way of example only, and are not intended to limit the scope of the inventions. Indeed, the novel embodiment described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A defect analyzing method of analyzing a defect of a semiconductor device manufactured by a plurality of process steps, based on an inspection result obtained by an inspection process, comprising:

acquiring defect information having a position and a size of the defect and a waveform of a reflected light in a region including the defect, from the inspection result;

acquiring process step information including the process steps and processing contents thereof;

performing a plurality of process simulations of the semiconductor device based on the defect information with respect to each of the process steps;

performing a plurality of optical simulations on results of the process simulations to generate a plurality of simulated waveforms for each of the process steps;

calculating a similarity degree between the acquired waveform of the reflected light and the simulated waveform for each of the process steps; and judging whether or not the calculated similarity degree exceeds a threshold value registered in advance to find out a causal process among the process steps.

2. The method according to claim 1, further comprising:

acquiring at least one of a film thickness and an etch rate of the semiconductor device; and replacing at least one of a film thickness and an etch rate of the processing content included in the process step information with the acquired film thickness or etch rate.

3. The method according to claim 1, wherein the process simulation is performed by forming a nucleus to be a factor of the defect in at least one process step or more in the plurality of process steps.

4. The method according to claim 3, wherein the nucleus is formed with a material used in manufacturing the semiconductor device.

5. A defect analyzing apparatus to analyze a defect of a semiconductor device manufactured by a plurality of process steps in a manufacturing apparatus, based on an inspection result obtained by an inspection apparatus, comprising:

a first acquiring unit configured to acquire defect information having a position and a size of the defect and a waveform of a reflected light in a region including the defect, from the inspection apparatus;

a second acquiring unit configured to acquire process step information including the process steps and processing contents thereof;

a first simulation unit configured to perform a plurality of process simulations of the semiconductor device based on the defect information with respect to each of the process steps;

a second simulation unit configured to perform a plurality of optical simulations on results of the process simulations in said first simulation unit to generate a plurality of simulated waveforms for each of the process steps;

a similarity calculating unit configured to calculate a similarity degree between the waveform of the reflected light acquired in said first acquiring unit and the simulated waveform for each of the process steps generated in said second simulation unit; and a judging unit configured to judge whether or not the similarity degree calculated in said similarity calculating section exceeds a threshold value registered in advance to find out a causal process among the process steps.

\* \* \* \* \*